(12) United States Patent
Shaw et al.

(10) Patent No.: US 6,221,055 B1
(45) Date of Patent: Apr. 24, 2001

(54) RETRACTABLE DENTAL SYRINGE

(75) Inventors: Thomas J. Shaw, Little Elm; Ni Zhu, Plano, both of TX (US)

(73) Assignee: Retractable Technologies, Inc., Little Elm, TX (US)

( * ) Notice: Subject to any disclaimer, the term of this patent is extended or adjusted under 35 U.S.C. 154(b) by 0 days.

(21) Appl. No.: 09/410,301

(22) Filed: Oct. 1, 1999

Related U.S. Application Data

(63) Continuation-in-part of application No. 09/034,411, filed on Mar. 4, 1998, now Pat. No. 5,997,512.

(51) Int. Cl.[7] .................................................. A61M 5/00
(52) U.S. Cl. ........................ 604/232; 604/195; 604/218
(58) Field of Search .................................. 604/232, 195, 604/218, 187, 110, 234, 236

(56) References Cited

U.S. PATENT DOCUMENTS

| | | |
|---|---|---|
| 3,306,290 | 2/1967 | Weltman . |
| 4,194,505 | 3/1980 | Schmitz . |
| 4,316,436 | 2/1982 | Schmitz et al. . |
| 4,413,991 | 11/1983 | Schmitz et al. . |
| 4,820,275 | 4/1989 | Haber et al. . |
| 4,927,414 | 5/1990 | Kulli . |
| 5,019,044 | 5/1991 | Tsao . |
| 5,084,018 | 1/1992 | Tsao . |
| 5,188,599 | 2/1993 | Botich et al. . |
| 5,330,430 | 7/1994 | Sullivan . |
| 5,330,440 | 7/1994 | Stanners et al. . |
| 5,385,551 | 1/1995 | Shaw . |
| 5,405,326 | 4/1995 | Haber et al. . |
| 5,423,758 | 6/1995 | Shaw . |
| 5,478,316 * | 12/1995 | Bitdinger et al. ................. 604/232 X |
| 5,501,670 * | 3/1996 | Sak .................................... 604/195 X |
| 5,613,952 | 3/1997 | Pressly, Sr. et al. . |
| 5,632,733 | 5/1997 | Shaw . |
| 5,634,909 * | 6/1997 | Schmitz ........................... 604/232 X |
| 5,681,292 | 10/1997 | Tober et al. . |
| 5,800,403 | 9/1998 | Pressly, Sr. et al. . |
| 5,891,104 | 4/1999 | Shonfeld et al. . |
| 5,957,897 * | 9/1999 | Jeffrey .............................. 604/232 X |
| 5,997,512 | 12/1999 | Shaw . |

* cited by examiner

*Primary Examiner*—J Yasko
(74) *Attorney, Agent, or Firm*—Locke Liddell & Sapp LLP

(57) ABSTRACT

A single use retractable medical device dispenses fluids from a separable carpule. A retraction mechanism having a spring loaded needle holder with a double ended needle is mounted in the front of a housing by means of a push ring (separable member) slidingly mounted on a widened portion of the needle holder. An outer edge of the push ring grips or is restrained by the inner wall surface of the housing to hold the needle holder in place. A carpule positioned through an opening in back of the housing is operated by a plunger which drives a separable two-part piston to unload medicine from the carpule through the needle. At the end of an injection, the plunger is depressed further. The carpule moves forward to remove the push ring thereby freeing the needle holder for retraction into the carpule through the front opening of the carpule. As the needle is retracted into the housing from one end, the edge of the thumb cap of the plunger disappears into an opening at the opposite end of the housing. The back of the housing may have the traditional thumb ring or it may have a "disappearing" thumb cap which is received into a widened opening in the back of the housing to thwart removal.

25 Claims, 9 Drawing Sheets

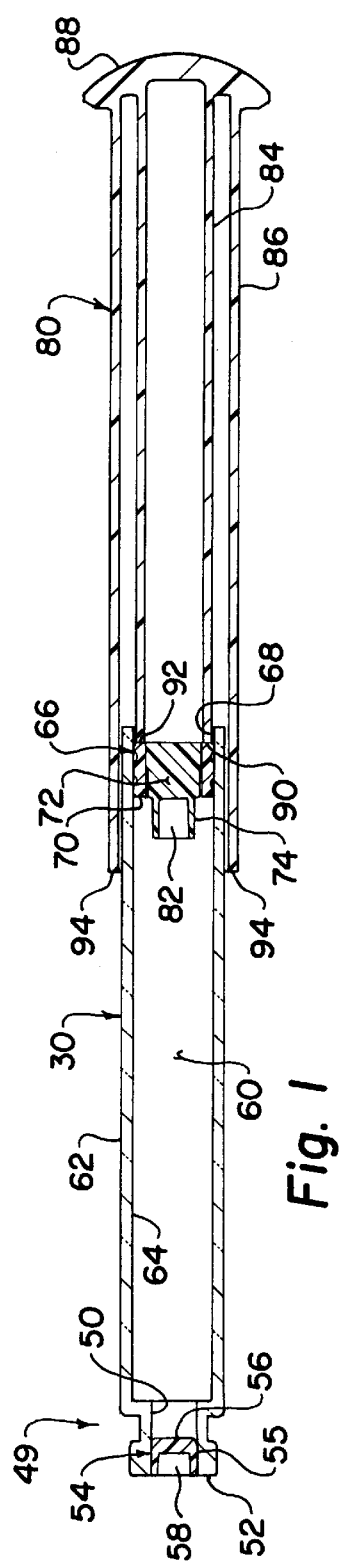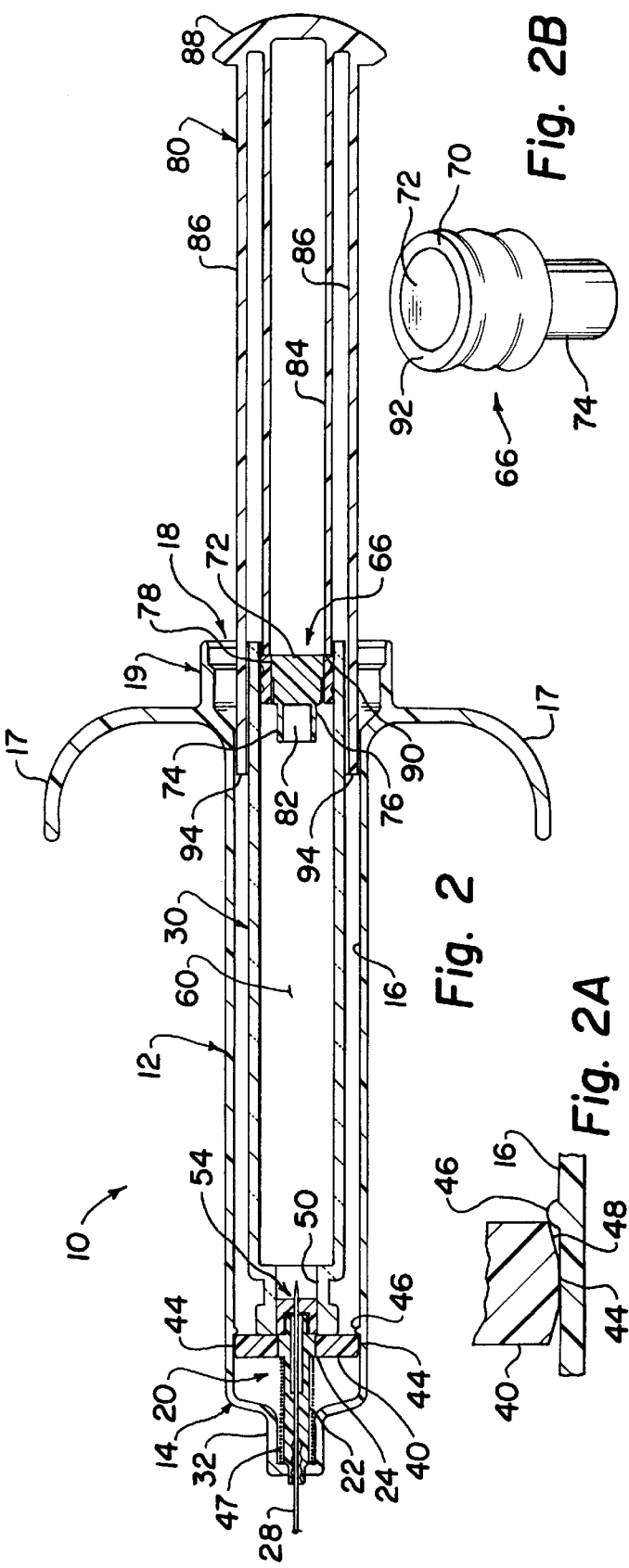

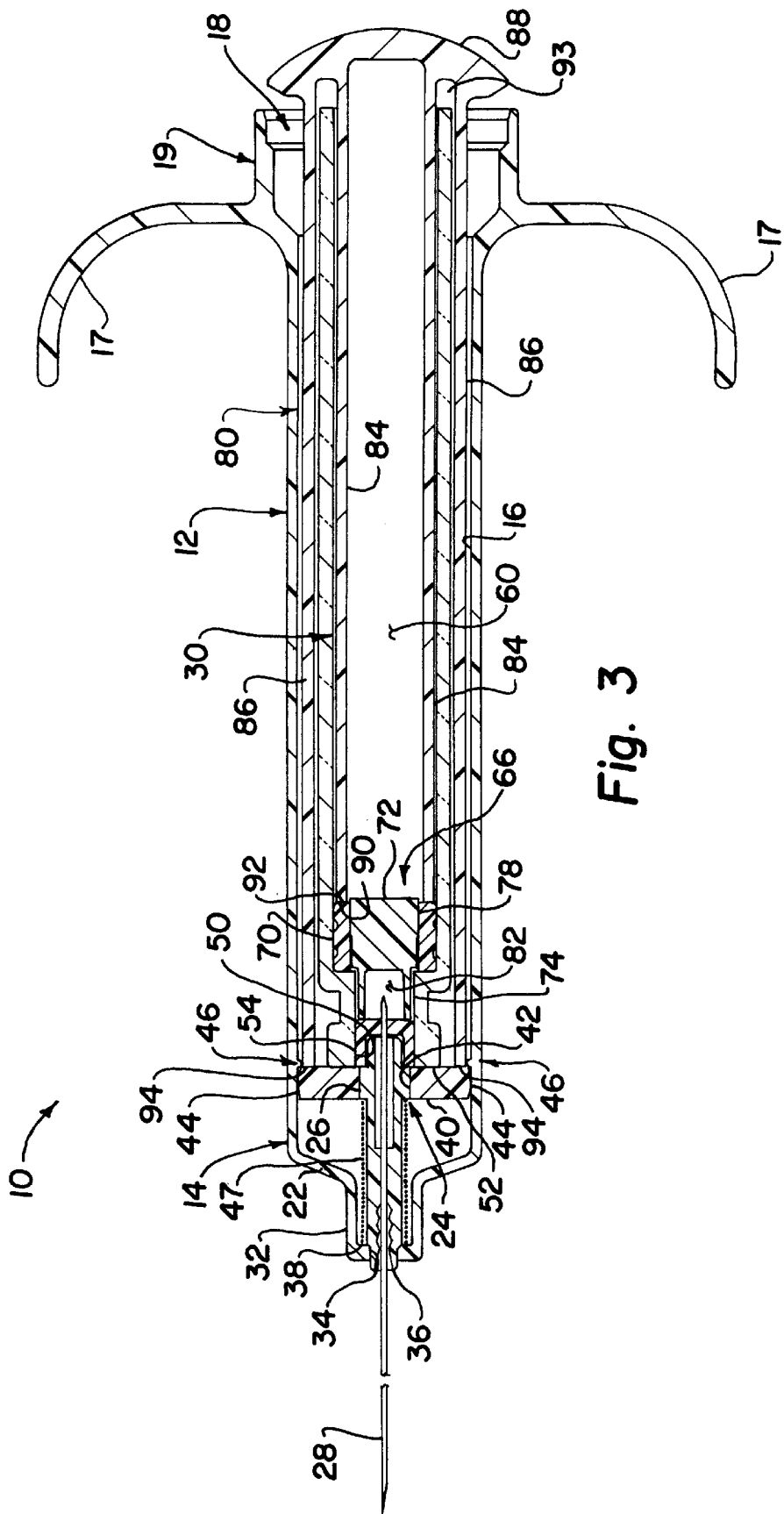

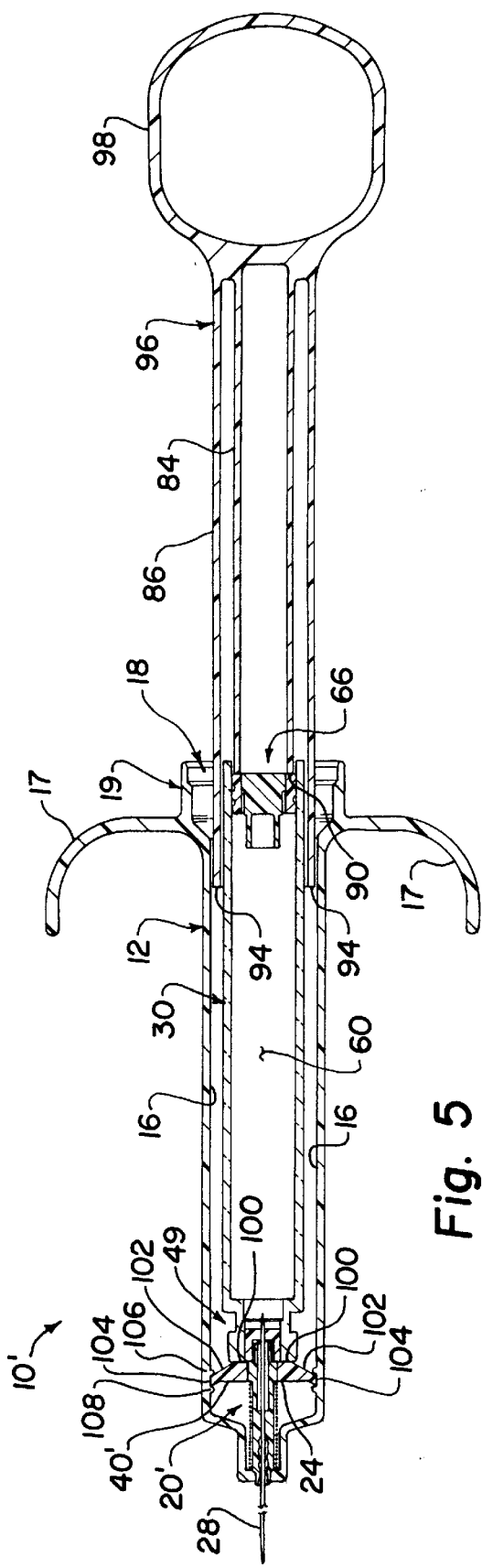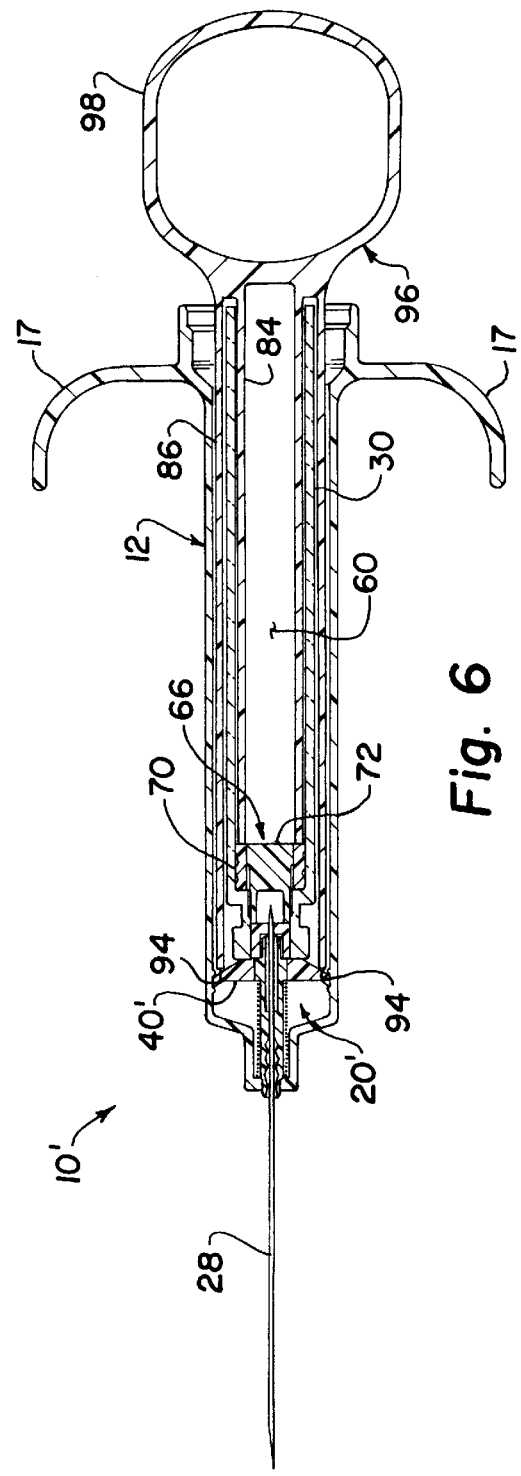

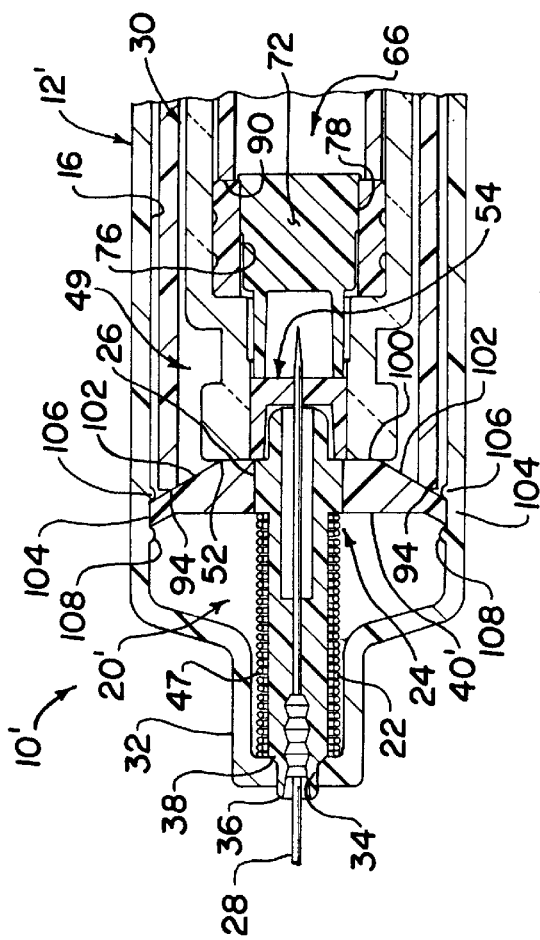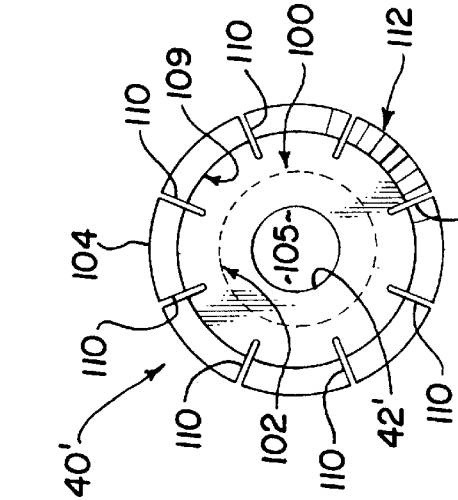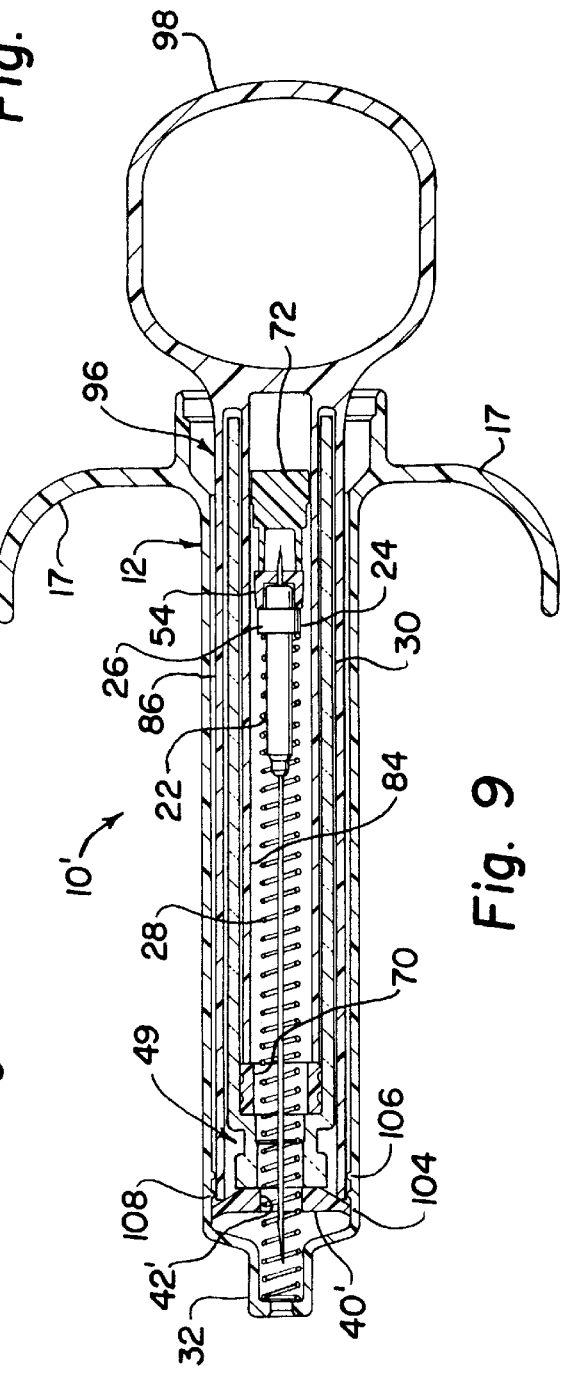
Fig. 8
Fig. 7
Fig. 9

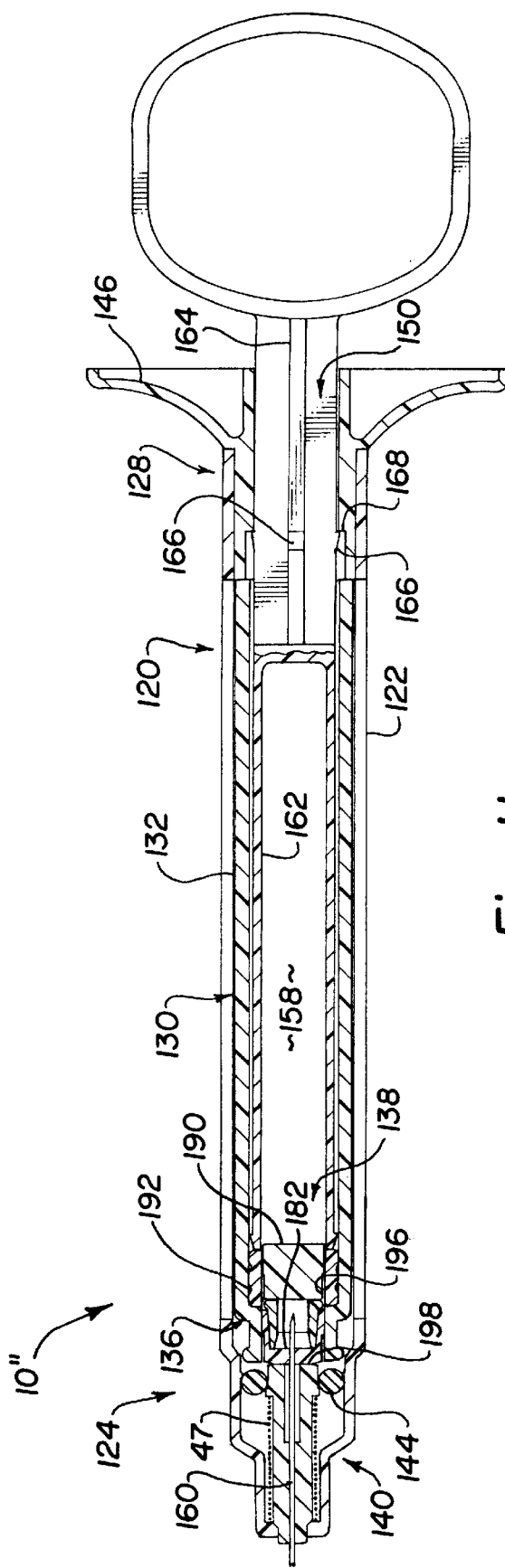
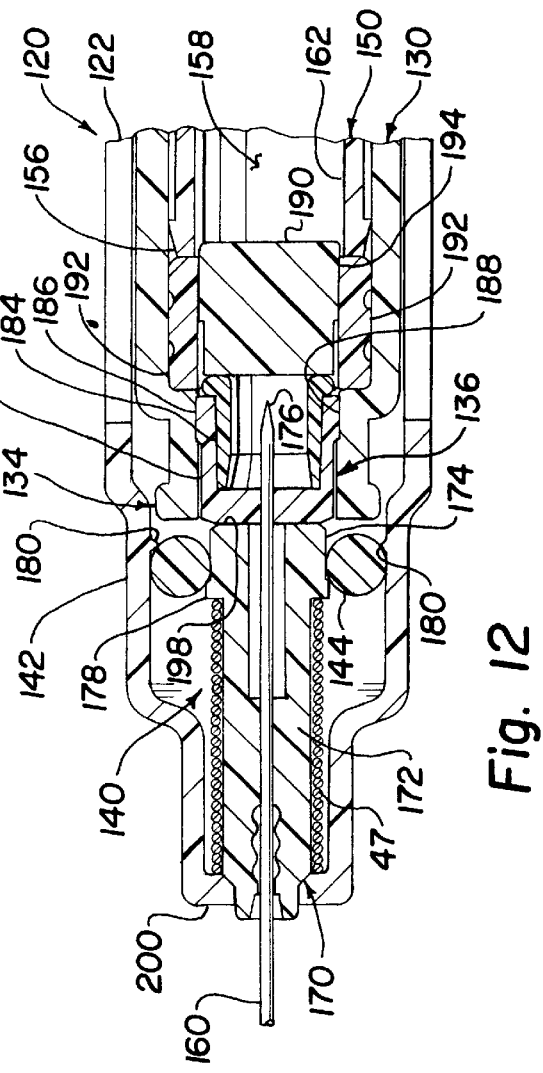
Fig. 11
Fig. 12

RETRACTABLE DENTAL SYRINGE

CROSS-REFERENCE TO RELATED APPLICATION

This is a continuation-in-part of prior patent application No. 09/034,411, filed Mar. 3, 1998, entitled "Retractable Dental Syringe" now U.S. Pat. No. 5,997,512 for which benefit under 35 U.S.C. § 120 is claimed.

FIELD OF THE INVENTION

The present invention is a retractable medical device, more particularly, a retractable device that employs a removable medicine container that is well suited for dental use.

BACKGROUND OF THE PRIOR ART

Conventional syringes have a barrel and a closely fitting piston which draws fluid into the barrel via a needle in front of the barrel. Fluid is drawn into the barrel through the needle, the air is expelled and an injection is made by depressing the plunger. Many of these medical devices have been designed to retract the needle by various mechanisms because of the continuing danger of exposed needles contaminated with infectious agents. With the increase of dangerous communicable diseases such as AIDS, it has become critical to eliminate needle stick injuries to medical personnel. Intensive efforts have been directed to development of retractable syringes which are safe, effective and practical, which can be mass produced at low cost.

Seemingly ignored in all this activity is the smaller but still significant group of syringes which employ a pre-filled cartridge of fluid medication and a double ended hypodermic needle communicating with the cartridge for injecting the contents of the cartridge. The pre-filled syringe cartridges are referred to as "carpules". They are typically cylindrical tubes with a puncturable membrane in front and a piston seal at the rear which is pressed forward by some form of plunger. The most common of these are the carpule syringes used by dentists in freezing the gums of their patients prior to their performing dental work on their teeth. Typically, the syringe enclosures with which such pre-filled syringe cartridges are used are not easily capable of retracting the needle into a protective enclosure to avoid inadvertent and potentially harmful needle sticks. Consequently, most syringes used for this purpose by dentists have a fixed needle which must be sheathed.

The relatively few attempts that have been made to produce a retractable needle syringe have produced results not altogether satisfactory. Weltman, U.S. Pat. No. 3,306,290; Sullivan, U.S. Pat. No. 5,330,430; and Haber, U.S. Pat. No. 4,820,275 among other things suffer from the deficiency that the device is necessarily much longer than the stroke the plunger itself would require in order that the outer shell house both needle and cartridge. Stanners, U.S. Pat. No. 5,330,440, although it doesn't suffer from the length deficiency, employs special thread engaging plugs in both ends of the carpule and plunger. These threaded connections must be mechanically connected together to withdraw the needle to the back of the special carpule. Retraction is done manually by disengaging a catch.

Although the needles can be retracted, these devices do not provide instantaneous retraction of the needle automatically at the end of an injection by further depression of the plunger while the needle is still in the patient's tissue. A slow controlled manual retraction of the needle is undesirable. Unintended movement of the syringe could damage tissue. Carpule syringe devices that would meet the above objections and which enable instantaneous retraction by continuation of the same motion used for the injection would be a significant improvement. These and other objects are the subject of the present invention.

SUMMARY OF THE INVENTION

The present invention is a single use retractable medical device which employs a modified carpule having a two-part sliding piston seal in back and a sliding seal in front. The retractable medical device is especially well suited for use as a dental syringe and one embodiment employs a thumb ring at the back of the plunger as is typical with dental syringes. The syringe is designed to retract after the injection by the simple expedient of continued depression of the plunger without moving the syringe away from the patient. The retraction parts and most of the needle are retracted into the carpule. All of the needle is retracted into the housing instantaneously upon depression of the plunger after the injection.

The carpule is unconventional mainly in the closures at the front and back end. The carpule has a cylindrical wall defining a fluid chamber and a front end with an opening into the fluid chamber and an open back end. A slidable front seal is lodged in the opening of the front end. The conventional carpule has no need for a sliding seal to cover the opening of the front end which is punctured by a rearwardly extending needle when the carpule is inserted. The modified carpule has a two-part sliding piston seal lodged in the open back end. The piston seal comprises an outer rim portion in sliding sealed contact with the wall of the fluid chamber and a slidably removable core portion. The sliding piston seal is moved by a plunger to the front of the fluid chamber to dispense all fluid. When driven in a retraction direction, the sliding front seal removes the core of the piston seal and traverses through the rim portion to enter the chamber along with following portions of a retraction mechanism.

The retractable medical device has a tubular housing having a wall defining a front end portion, a main body portion, an open back end and an inner surface defining a hollow interior. A retraction mechanism is mounted in the front end portion of the housing. The retraction mechanism comprises a needle holder having an elongated body with a front, a back and a widened part of the body spaced behind the front. Needle portions extend from the front and back of the needle holder. A spring is mounted under the widened part of the needle holder to apply retraction force thereto.

A releasable "push ring" is grippingly mounted around the widened part of the needle holder along a longitudinal interface. The push ring extends radially outwardly to the inner wall of the housing. Outer edges of the push ring are preferably in sliding gripping contact with the housing to hold the needle holder in place against the retraction force provided by the spring. The housing wall may be provided with stops behind the push ring to prevent rearward motion of the push ring and retraction mechanism. One form of push ring is a separable member shaped like a disc with a relatively straight walled opening in the center and a rounded outer edge. Another form of separable member is essentially an "O" ring which is donut shaped or still further a donut shaped "O" ring with a relatively straight walled central opening and a curved outer edge. The push ring/separable member holding the needle in place is not required to perform a sealing function for fluid due to the fact that the carpule holds the medicinal fluid. This means that the push ring/separable member could have a hub and spoke design or segmented structure of many different kinds.

A carpule of the type described above is inserted into the housing with the front seal in contact with the back end of the needle holder and punctured by the needle. The front of the carpule faces the push ring. One form of plunger is adapted to progressively receive the carpule while entering the housing and pressing the slidable piston forward to dispense fluid through the needle. Another form of plunger is received within the carpule in the manner of an ordinary syringe plunger in its housing.

On one form of plunger, a wall part presses the outer rim part of the piston seal so that the core portion can slide rearwardly relative to the rim portion during retraction without being obstructed by the plunger. This form of plunger also has another wall part which presses against the outer edge portions of the push ring when the piston seal is fully depressed to the front of the carpule at the end of an injection. This outer wall part is outside the carpule near the wall of the tubular housing. It engages the outer part of the push ring after the carpule is emptied. Retraction occurs by further depression of the plunger to move the push ring from a widened part of the needle holder while dislodging the front seal and the separable core part of the piston seal. Forward movement of the carpule against the needle holder frees the front seal and core part of the rear piston seal so that retraction force drives the needle holder and needle through the front opening into the carpule where they are safe. The carpule and the push ring are moved into a necked end part at the front of the housing simultaneously allowing a thumb cap to enter the back of the housing where the edge cannot be reached. It may be said to "disappear" within the housing. In an alternate version of the plunger, a traditional thumb ring is used in place of the thumb cap. Although the thumb ring allows withdrawal of the plunger after retraction, the parts cannot be reassembled for reuse because there is virtually no way to retrieve the outer rim portion of the piston which is lodged next to the wall just behind the front opening.

An alternate needle holding structure comprises a dish shaped push ring having a center body portion with a forwardly angled outer rim portion in contact with the wall of the housing and an opening with interfacing surfaces which slidingly grips the widened part of the needle holder. The housing has a small stop structure positioned under the push ring to provide overcomable resistance to movement thereof. The alternate version of the push ring tends to jam or bind the outer rim or edge against the wall of the housing because of a slight degree of flexing purposefully provided wherein the center moves forward slightly with respect to the edges which are held by the stop structure. This tends to prevent force imposed by the carpule by depression of the plunger during an injection from prematurely releasing the push ring from the needle holder. At the "end of injection" position, the plunger has an outer wall which lies along the wall of the housing pressing against the outer edge portion of the push ring. Forward movement of the plunger releases the edge of the push ring from the locking surfaces so that the push ring may be removed easily. The angled outer rim portion may have angled segments which help interact with the stop structure on the inner wall surface of the housing to hold the push ring in place until it is released by the plunger.

In an alternative structure, the carpule is adapted to substantially occupy the space within the tubular housing with the mouth of the carpule positioned to remove a releasable part from the retractable needle structure by moving forward. The depressible plunger enters the tubular housing from the rear and empties the carpule by moving the rear seal forward to an end-of-injection position of the two part seal. The plunger pushes against one part of the two part seal which has previously been described as a rim portion. The plunger is received entirely within the carpule. Upon continued depression of the plunger after the end-of-injection position, the carpule moves forward with the plunger, the front seal is pushed back by the retractable needle structure and the carpule itself removes the separable member from the needle holder which allows the needle holding part to automatically retract into the carpule through the mouth of the carpule. The releasable and separable part of the needle holding structure may be the "O" ring embodiment or the disc like member with a relatively straight walled opening in the center and a rounded outer edge.

The parts are relatively uncomplicated and subject to mass production and automated assembly. The push ring may be assembled with the unneedled needle holder in an upright position, the spring placed on the needle holder and the housing dropped over the assembled parts to compress the spring as the push ring and needle holder is moved forward. The needle can be inserted from the front. This is the first practical retractable dental carpule syringe which retracts by continuation of the same motion used for injection and which retracts the needle directly from tissue to eliminate risk of needle stick with a contaminated needle. It uniquely employs the used carpule to receive the contaminated needle.

BRIEF DESCRIPTION OF THE DRAWINGS

FIG. 1 is a longitudinal cross section through the center of the carpule and plunger in the initial assembled position;

FIG. 2 is a cross section through the retractable medical device with the retraction mechanism mounted in front of the housing and the front of the carpule positioned behind the push ring with the front seal punctured by the double-ended needle;

FIG. 2A is an enlarged area of the outer edge of the push ring and wall of the housing showing an annular ring which slightly reduces the inside diameter to help hold the push ring and needle holding assembly from moving in the direction of retraction;

FIG. 2B is a perspective view of the two part sliding piston seal which is lodged in the back opening of the carpule seen in cross section in FIG. 2;

FIG. 3 is a cross sectional view along the center-line of the retractable medical device of FIG. 2 after the plunger has been depressed to expel substantially all fluid from the chamber of the carpule in the position that results at the end of an injection;

FIG. 5 represents a longitudinal cross sectional view through the center line of an alternative variation of the retractable medical device showing a forwardly angled dish shaped push ring with edges positioned between annular constrictions on the inner wall of the housing in the ready to inject position;

FIG. 6 shows the retractable medical device of FIG. 5 after the plunger has been depressed to a first position where substantially all fluid is dispensed from the carpule and part of the plunger has reached the outer edge of the push ring where further depression of the plunger will trigger retraction;

FIG. 7 illustrates an alternative design for the dish shaped push ring of FIGS. 5–9 showing forwardly angled segments comprising the angled outer rim of the alternate push ring which are more easily flexed to facilitate jamming of the push ring in opposition to forward movement;

FIG. 8 is an enlarged cut away cross sectional view of the front portion of the medical device of FIG. 6 showing the plunger in a position to prevent deflection and jamming of the angled edges of the push ring against the stop structures formed on the inner wall of the housing;

FIG. 9 is a cross sectional view of the retractable medical device of FIGS. 5, 6 and 8 after the plunger has been depressed beyond the position of FIG. 8 to cause relative movement of the push ring and carpule relative to the needle holder and create a passage for the retraction of the needle holder and needle shown in the fully retracted position;

FIG. 11 is an enlarged cross sectional view of the alternate device of FIG. 10 wherein the plunger has moved to the front of the carpule at the end-of-injection position;

FIG. 12 is an enlarged view of the front of FIG. 11 shown immediately before retraction is initiated;

DETAILED DESCRIPTION OF THE INVENTION

Figure 4:
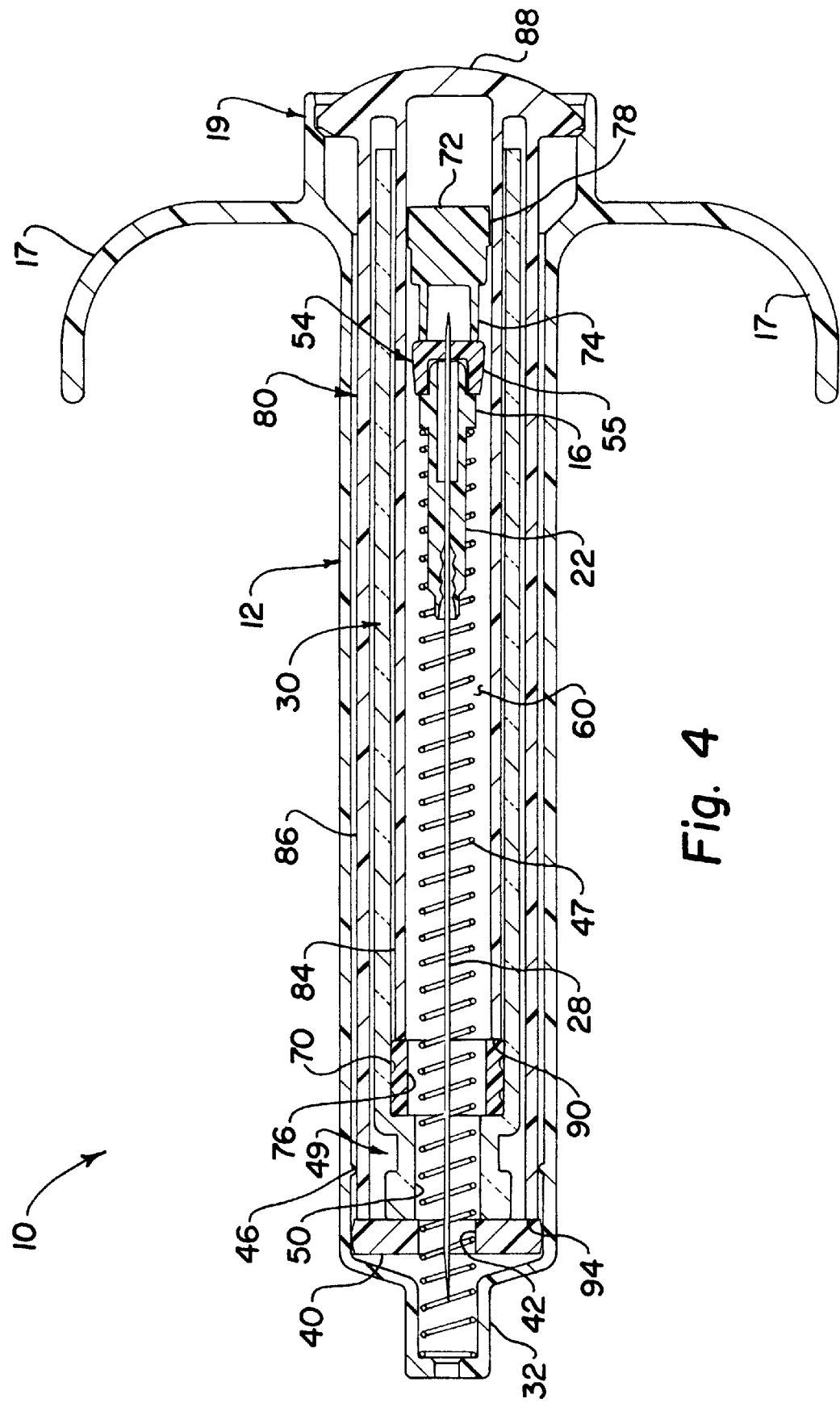
FIG. 4 represents the retractable medical device of FIG. 3 in a cross sectional view after the plunger has been depressed further from the fully injected position of FIG. 3 to show the fully retracted position of the needle-holding structure into the carpule.

In the description that follows the same parts will be referred to with the same reference numerals and like parts may be indicated by applying a prime mark (') to reference numerals. A retractable medical device 10 is shown in FIG. 2 in the ready to use position. Tubular housing 12 has a front portion 14, an inner wall surface 16, and an open back end 18. Open back end 18 has a widened portion 19 to receive the thumb cap 88 on the back of a plunger 80 having a pair of finger grips 17.

A retraction mechanism 20 is mounted in front portion 14 of housing 12. Seen better in FIG. 3, retraction mechanism 20 comprises elongated needle-holder body 22 with a widened part 24 having an outwardly facing surface 26 of limited length. Needle holder 22 circumscribes and holds a double-ended needle 28 which provides a fluid path into a carpule 30 to be described. Needle 28 may be a continuous needle as shown in FIG. 3 or fluidly connected separate portions having a forwardly and rearwardly extending portion to respectively engage tissue and engage a medicine supply in carpule 30. Front portion 14 of housing 12 includes a reduced diameter nose 32 having an opening 34 for front end 36 of needle holder 22. Front end 36 is a reduced diameter from body 22. It and the flange on nose 32 serve as a seat 38 for needle holder 22 in nose 32. Needle holder 22 is held in place by means of push ring 40 having a central opening with an inwardly facing surface 42 which grippingly holds outwardly facing surface 26 of widened part 24. Push ring 40 has an outer rim or edge 44, here shown to be arcuate, preferably held in slidable, gripping contact with inner wall 16 of housing 12. An annular stop 46 comprising a slightly raised portion of inner surface 16 may be used to prevent rearward movement of the retraction mechanism.

It is preferable that stop 46 allow the slightly resilient edge of push ring 40 to be forced over it as the push ring slides forward during installation of retraction mechanism 20 from the back of the housing. It is also contemplated that stop 46 could be a larger stop that requires push ring 40 to be installed from the front of housing 12. In that case, housing 12 would be a two-part housing instead of a unitary housing as now shown in the drawings. It could have a detachable front part which is attached to the cylindrical housing after the retraction mechanism is installed. The stop could be individual inwardly radial protrusions or separated segments which prevent push ring 40 from moving in a retraction direction. A seat created by widened portion 24 receives the end of a biasing means in the form of compressed spring 47 which applies a retraction force against needle holder 22.

Turning now to FIGS. 1, 2 and 2A, the outer edge 44 of push ring 40 is seen to be a relatively flat spot in the center with angled portions 48 on either side. The reduction in contacting surface area tends to increase the unit pressure at the interface between the push ring 40 and inner wall 16 and tends to compensate to some extent for manufacturing tolerance variations.

Referring now to FIG. 1, carpule 30 has a reduced diameter front portion 49 having a relatively short opening 50 and a front surface 52. A slidable front seal 54 is lodged at the front of opening 50. Front seal 54 is a cup shaped member having a solid back 56, sides 55 in contact with the opening and an open side which serves as a socket 58. The side 55 may have an arcuate profile in its uncompressed state shown in FIG. 4. This may be configured to adjust the amount of sliding friction it takes to move seal 54 along the wall surface of opening 50.

A medicament chamber 60 is defined between the front portion 49, the elongated tubular wall 62 having an inner surface 64 and a slidable piston seal 66. The back of chamber 60 is defined by slidable two-part piston seal 66 lodged in opening 68 at the rear of carpule 30. Sliding piston seal 66 shown in FIG. 2B comprises outer rim member 70 and releasable core member 72 having a forwardly extending wall portion 74. Better seen in FIG. 2, rim member 70 is a cylindrical seal of suitable length having an opening comprising inwardly facing surface 76 therethrough. It is a sleeve which circumscribes releasable core member 72.

Core member 72 contacts inner surface 76 at land 78. Land 78 comprises a longitudinal surface which contacts rim 70 along a length which is less than the length of inwardly facing surface 76. Alternatively, the land could be a raised portion of rim member 70 and core member 72 could have a uniform cylindrical surface. The length of land 78 and the composition and fit of slidable core member 72 is selected so the two part piston seal will remain intact in the face of internal pressure generated in chamber 60 when a plunger 80 is depressed. The forwardly extending wall 74 of slidable core 72 is shown as cylindrical although it could be a plurality of individualized projections or legs which form a socket like opening 82. Socket 82 will receive the back end of needle 28. Wall portion 74 is adapted to fit inside opening 50, comprising the mouth of the carpule, and extend forwardly to contact front seal 54. This forward extension 74 of core member 72 allows the front seal member 54 and core member 72 to move together as a unit as retraction is being initiated. That way they are both in position to come free when needle holder 22 is released.

Returning now to FIGS. 1 and 2, plunger 80 has an inner wall 84 and an outer wall 86, parallel and spaced apart. These walls are preferably tubular for stability. Inner wall 84 and outer wall 86 may be connected at the back by a disappearing thumb cap 88 which will be closely received in widened part 19 of back opening 18 of housing 12. Inner wall 84 terminates in end surface 90 which is adapted to engage end surface 92 of rim member 70 seen in FIG. 2B. Inner wall 84 is adapted to closely enter opening 68 of the carpule with surface 90 in contact with surface 92 but not in contact with any portion of releasable core member 72. Outer wall 86 is adapted to progressively receive carpule 30 while entering housing 12 as plunger 80 is depressed to move two-part piston seal 66 forward from the position of FIG. 2 to the end of injection position of FIG. 3. Outer wall 86 is closely received by inner wall 16 to provide some lateral stability to the assembled plunger and carpule as they are introduced. Outer wall 86 is preferably longer than inner wall 84 to partially engage the back end of the carpule in the manner shown in FIG. 1. This facilitates insertion of the carpule and plunger into the housing. End 94 of outer wall 86 stabilizes the combined carpule and plunger by virtue of sliding contact along wall surface 16.

More importantly, the relative length of the inner and outer walls 84, 86 of plunger 80 are such that piston seal 66 bottoms out in the front portion of carpule 30 at about the same time as circular end 94 reaches the outer edge portion of push ring 40 in preparation for retraction. Further depression of plunger 80 causes movement of carpule 30 as well as the plunger relative to the housing and allows outer wall 86 of the plunger and/or the front 52 of the carpule to remove push ring 40 from needle holder 22, which is grounded in the housing. The back end of needle holder 22 fits in socket 58 with the rear portion of needle 28 extending through seal 54. The back end of needle holder 22 may have a diameter smaller than socket 58 to control the amount of frictional engagement between side surface 55 and surface 50 or the combined diameter of the sides of socket 58 and back of needle holder 22 may be so designed. Socket 58 helps front seal member 54 remain on the back of needle holder 22 during retraction without getting crosswise or causing a jam and also helps align the carpule with the needle holder. When plunger 80 is depressed further beyond the end of injection position shown in FIG. 3, the plunger moves the push ring while substantially and simultaneously moving carpule 30 relative to the housing. Movement of the carpule beyond the end of injection position of FIG. 3 causes movement of rim member 70 relative to core member 72 and front seal 54 in preparation for retraction. Needle holder 22, front seal 54, and core member 72 are adapted to contact each other when plunger 80 is depressed sufficiently to bottom out piston seal 66 in carpule 30, a position which has expelled substantially all fluid from chamber 60 through needle holder 22.

An alternate retractable medical device is designated retractable medical device 10' in FIGS. 5–9. Device 10' in FIG. 5 employs most of the same parts as the retractable medical device shown in FIGS. 1–4. Tubular housing 12 having an inner wall surface 16 is shown loaded with carpule 30 as before described. A modified plunger 96 differs from plunger 80 in that thumb cap 88 is replaced with thumb ring 98. This is more like the plunger dentists are used to but does not have the nonreusable feature of the syringe having the disappearing thumb cap. Plunger 96 has the same inner wall 84 and outer wall 86 as plunger 80 designed the same way to operate two-part sliding piston seal 66 to expel fluid from chamber 60. Structure 10' differs from structure 10, with the exception of the thumb ring, by an alteration to the retraction mechanism. Retraction mechanism 20' is otherwise identical to mechanism 20 except for the substitution of push ring 40' for push ring 40. Push ring 40' has a center body portion 100 which in FIG. 5 is shown slightly smaller in diameter than the diameter of front portion 49 of carpule 30. Push ring 40' has a forwardly angled outer rim portion 102 having an outer edge 104 in contact with inner wall surface 16.

Turning now to the enlarged view of FIG. 8, stop structure 106, 108 preferably comprises annular protrusions 106, 108 on inner surface 16 of housing 12'. Protrusions 106, 108 are the only difference between housing 12 and 12' whereby stop structures 106, 108 are placed above and below outer edge 104 of angled portions 102. When force is imposed on center portion 100 during an injection by front surface 52 of carpule 30, carpule 30 tends to jam the outer end 104 of outer rim portion 102 by slight flexing outwardly of alternate push ring 40'. At the end of the injection (the position of FIG. 8), further depression of modified plunger 96 pushes the outer rim portion of push ring 40' away from the stop structure so that push ring 40' can then be removed from widened part 24 of needle holder 22. This movement simultaneously causes motion of carpule 30 and rim member 72 relative to sliding front seal 54 and removable core portion 72 of two-part slidable piston seal 66. Modified plunger 96 and push ring 40' move forward while grounded needle holder 22 remains in place. The thickness and shape of push ring 40' is selected to function this way. A slight degree of flexibility through material or thickness variations is preferred to assure the jamming action occurs in response to force imposed by carpule 30 without removal of push ring 40'. FIG. 9 shows the result upon further depression of modified plunger 96 from the position of FIG. 8 where it can be seen that push ring 40' has been demounted by being moved forward by force imposed by the front portion of carpule 30 and outer wall 86. This has moved push ring 40' forward demounting it from widened part 24 of needle holder 22 and contemporaneously driven the stacked front seal and core member 72 rearwardly in the carpule where they are retained.

FIG. 7 is a variation of push ring 40' of FIG. 8 showing extreme outer edge 104 and a central opening 105 with an inwardly facing surface 42'. Surface 42' slidingly grips surface 26 where it is held by needle holder 22 in opposition to compressed spring 47. This is preferably a frictional engagement. Center body portion 100 in FIG. 7 is represented by that portion between surface 42' and the dotted circle. The portion outwardly from the dotted circle is the forwardly angled outer rim portion 102 which may have additional change of direction 109. Flexibility of push ring 40' can be increased by adding a plurality of segmenting grooves 110, spaced evenly around the periphery, extending radially through most of angled portion 102. Additionally, a plurality of radial separations 112 may be added to increase flexibility of the outer edge.

In operation, the back end of carpule 30 is associated with the front of the plunger as shown in FIG. 1. Then the plunger and carpule assembly is introduced into open back end 18 of housing 12 and carpule 30 is moved forward until seal 54 is punctured by the rearwardly extending portion of needle 28 and some resistance is felt as the front of the carpule bottoms out against push ring 40. Socket 58 in sliding front seal 54 receives the back end of needle holder 22. The medical device is now in the initial position of FIG. 2 ready for use.

As needle 28 is inserted into a patient, plunger 80 is depressed to inject the contents of chamber 60 through needle 28. Push ring 40 grips the needle holder tightly enough to resist force imposed on the carpule by depression of the plunger. When the plunger is depressed to empty the carpule, two-part piston seal 66 comes to bottom against a reduced diameter back of front portion 49. This brings end 94 of outer wall 86 in contact with the outer edge portion of ring member 40. At this point, wall portion 74 of member 66 has entered opening 50 and is in contact with back wall 56 of sliding front seal 54. This position is referred to as the end of injection position which is shown in FIG. 3.

Further depression of the plunger will cause retraction of the needle from the patient in one quick motion with the needle being withdrawn into the housing and the retractable parts lodged in the carpule. As the plunger is depressed, inner wall 84 pushes against rim 70 which is bottomed in the front of the carpule. Simultaneously, outer wall 86 pushes against the outer edge portions of push ring 40 to begin sliding the push ring forward off needle holder 22. The combined action of the front of the carpule and the outer wall of the plunger slides the push ring forward along the interface 26, 42. At the same time, forward movement of front seal 54 and core member 72 is prevented by needle holder 22 which is grounded in the housing. Since rim member 70 is restrained by inner wall 84 which is moving forward with the carpule, the front seal member and core member can be seen as moving rearwardly as a unit relative to the carpule. When plunger 80 is moved forward enough to separate the push ring from the needle holder, the core member may be loose or nearly loose from the rim member. As push ring 40 frees the needle holder, the remaining pressure on thumb cap 88 instantly moves sliding seal 54 through opening 50 of front portion 49 of the carpule and spring 47 drives needle holder 22 and needle 28 through the opening of the mouth of the carpule into chamber 60 where they remain biased in the retraction direction. The edges of thumb cap 88 are closely received in widened opening 19 making it very difficult or impossible to remove the plunger or the now retracted components from housing 12.

It is evident the amount of movement necessary to remove push ring 40 may be altered by changing the length of the interfacing surfaces 26, 42 on the needle holder and push ring respectively. Although the push ring is preferably held on the widened part of the needle holder by friction along the interfaces 26, 42, it is also possible to employ an adhesive there which will break away under a predetermined force. Core member 72 is preferably frictionally engaged with rim member 70. The diameter of the mouth of the carpule and the core member must, of course, be large enough to allow the widened part of the needle holder and the sliding front seal the pass therethrough. Core member 72 must be held tightly enough within rim member 70 to withstand the pressure generated force imposed as the plunger is depressed during an injection.

The alternate embodiment of FIGS. 5–9 functions in a similar manner, the difference being an alteration of the push ring 40' and the provision of a stop structure 106, 108 which captures the edge 104 of push ring 40'. When force is imposed on the center portion by carpule 30, the dish shaped push ring tends to expand outwardly and bind more tightly against surface 16, including some binding effect on the widened part of needle holder 22. FIG. 5 shows the ready to inject position and FIG. 6 shows the end of injection position, comparable to FIGS. 2 and 3.

In FIG. 6, once end 94 of tubular wall 86 pushes against the outer edge portion of push ring 40', it releases edge portion 104 by relieving the binding condition. It can be configured to contact push ring 40' just before the piston seal bottoms out in the front of carpule 30 to facilitate releasing the edge of the push ring from the stop structure. As the edges of push ring 40' are released from the stop structure, the plunger and carpule move forward to remove the push ring from the needle holder and simultaneously slide the carpule forward with respect to the sliding front seal and core member 72 to reach the retracted position of FIG. 9 as before described. Like the previous embodiment, the embodiment of FIGS. 5–9 is intended as a single use product. Although the thumb ring of the alternate design makes it possible to remove the plunger after retraction, the parts are so disassembled as to be extremely difficult of reassembly. In particular, rim member 70 is stuck in the bottom of the carpule with no perceptible way to dislodge it.

A further improvement is illustrated by the syringe 10" illustrated in FIGS. 10–14 which differs in construction but functions in the same manner as the other embodiments in the way it is retracted. Although the structural changes from the previous embodiments are relatively small, different reference numerals are used in most cases to avoid confusion.

Figure 10:
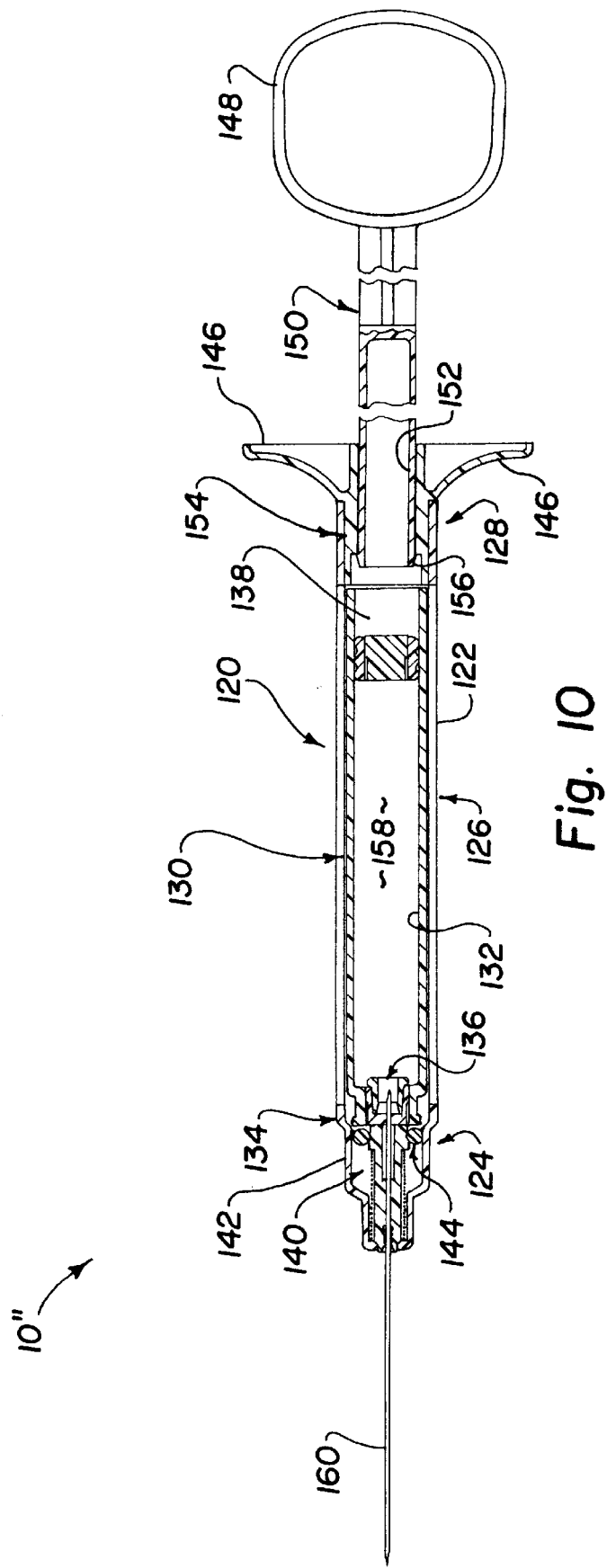
FIG. 10 is a cross sectional view of an alternative structure in which the mouth of the carpule removes the releasable part of the retractably mounted needle as the carpule is moved forward by the plunger after the contents are expelled.

In FIG. 10, syringe 10" has an elongated tubular housing 120. Tubular housing 120 has an elongated wall 122 forming a front portion 124, an intermediate portion 126 and a rear portion 128. Tubular housing 20 is adapted to accept a carpule 130. Carpule 130 differs from carpule 30 in that it is sized to substantially occupy intermediate portion 126 of housing 120. Wall 122 of carpule 130 preferably lies substantially adjacent the inside surface of wall 122 in the intermediate portion of the housing. Carpule 130 has a mouth 134, front seal 136 and two part rear seal 138. These parts will be described later in greater detail, but it suffices to say that they operate in essentially the same manner as the previously described front seal and two part rear seal of the carpule 30. A needle structure 140 is retractably mounted in front portion 124 of housing 120. A necked in or reduced diameter portion 142 of front portion 124 releaseably engages a releasable part 144 mounted in line with mouth 134 of carpule 130.

Rear end portion 128 of tubular housing 120 includes a grip 146 which is used in combination with a thumb ring 148 of a depressible plunger 150. Plunger 150 slidingly enters housing 120 through opening 152 in rear portion 128. Plunger 150 has a front end portion 154 having a hooked front 156 which can be seen to selectively engage one part of two part rear seal 138. Forward movement of seal 138 by means of plunger 150 is calculated to move the fluid from fluid chamber 158 of carpule 130 through needle 160 of needle structure 140. The back of this embodiment may have the "disappearing" handle like that of FIGS. 1–4.

FIGS. 11 and 12 in larger scale show more details of the structure of syringe 10" shown in FIG. 10. FIGS. 11 and 12 show the position of syringe 10" at the end-of-injection position like earlier structures shown in FIGS. 3 and 6. At the end position plunger 150 has been depressed forward toward needle structure 140 thereby moving two part seal 138 until it comes in contact with front seal 136. It is noted that plunger 150 has an elongated hollow tubular portion 162 which slides in proximity along the inside surface of wall 132 of carpule 130. A rear portion of plunger 150 may consist of a set of cross-shaped flanges 164 which may be equipped with unidirectional ramped stops 166 which engage an edge 168 at a change of diameter of rear portion 128. Unidirectional stops 166 prevent removal of the plunger 150 after the contents of carpule 130 have been emptied through needle 160. As this is a one use syringe, stops prevent disassembly by preventing removal of plunger 150 after syringe 10" has been used.

Referring now to FIG. 12, retractable needle holding structure 140 has a needle holder 170 having a needle holder body portion 172 having a widened part 174 comprising the head of the needle holder. Double ended needle (or two oppositely pointed needles in fluid communication) are fixed by an adhesive in body portion 172 with a rear end portion 176 piercing front seal 136. When plunger 150 is depressed, fluid in chamber 158 is discharged through needle 160. Widened part 174 of needle body 172 may be provided with an annular rim (or spaced rim portions) which tends to serve as a projection which operates in cooperation with annular rim 180 (which may comprise rim segments) on the inner wall of necked in portion 142 of housing wall 122. The embodiment shown employs a separable member in the form of an "O" ring made of a material which is compressible. The cooperating constrictions 178, 180 ensure that the "O" ring 144 must be compressed in order to allow needle body 172 to move rearwardly under the influence of compressed spring 47. It should be considered within the scope of the invention to have a separable part (144) which is a breakaway part or that an adhesive or some form of tenuous welding, such as by ultrasonics, could be used to temporarily connect the separable part with the needle holder.

In this embodiment front seal 136 comprises two interlocking parts comprising a cup shaped member 182 with the open part of the cup facing rearwardly and the bottom of the cup in contact with the top 198 of head 174 of needle body 172. A grommet-like member 184 is forced into the opening of cup shaped member 182 to slightly spread it and provide a seal with the inside opening of mouth 134. In particular, cup member 182 may include a rim 186 which may occupy a slight depression 188 in the otherwise smooth wall of mouth 134. The combination of rim 186 and depression 188 can have the beneficial effect of increasing frictional resistance to prevent premature removal of sliding seal 136 when plunger 150 is depressed to discharge fluid from carpule 130.

The two part rear seal is slightly different than previous sliding piston seal 66 in that it does not need the projecting portion 74. Sliding rear seal 138 has a removable core portion 190 and a slideable rim portion 192 wherein rim portion 192 is engaged by front 156 of plunger 150. Core portion 190 may include a land 194 wider than the rest of core 190 to help control the amount of friction required to remove core 190 from rim 192.

Everything is bottomed out in FIG. 12. Plunger 150 has pushed the rear seal forwardly into contact with the front seal. Only core portion 190 is in line with front seal 134 for dislodgment. The smaller diameter of mouth 134 creates a ledge 196 which prevents further forward movement of the rear seal rim member. Cup portion 182 is bottomed against top 198 of needle holding body 172 which in turn is bottomed in the front 200 of a further constricted portion of tubular body 120. Since the needle holder is bottomed in the housing and rim member 192 is bottomed in carpule 130, further depression of plunger 150 moves the carpule forward in relation to front seal 136 and core member 190 which move in tandem through the mouth of the carpule as the carpule moves forward to remove separable ring member 144 from needle body 172 to free the needle.

Figure 12A:
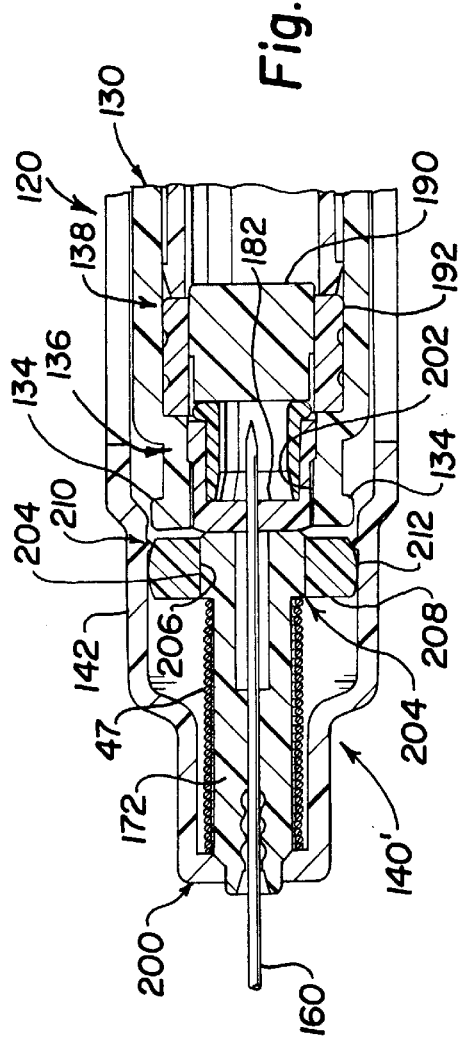
FIG. 12A is an enlarged view of the structure of FIG. 12 in which the separable part of the retractably mounted needle is a disc-like member having a substantial linear inner face holding the head of the needle holder.
Figure 13:
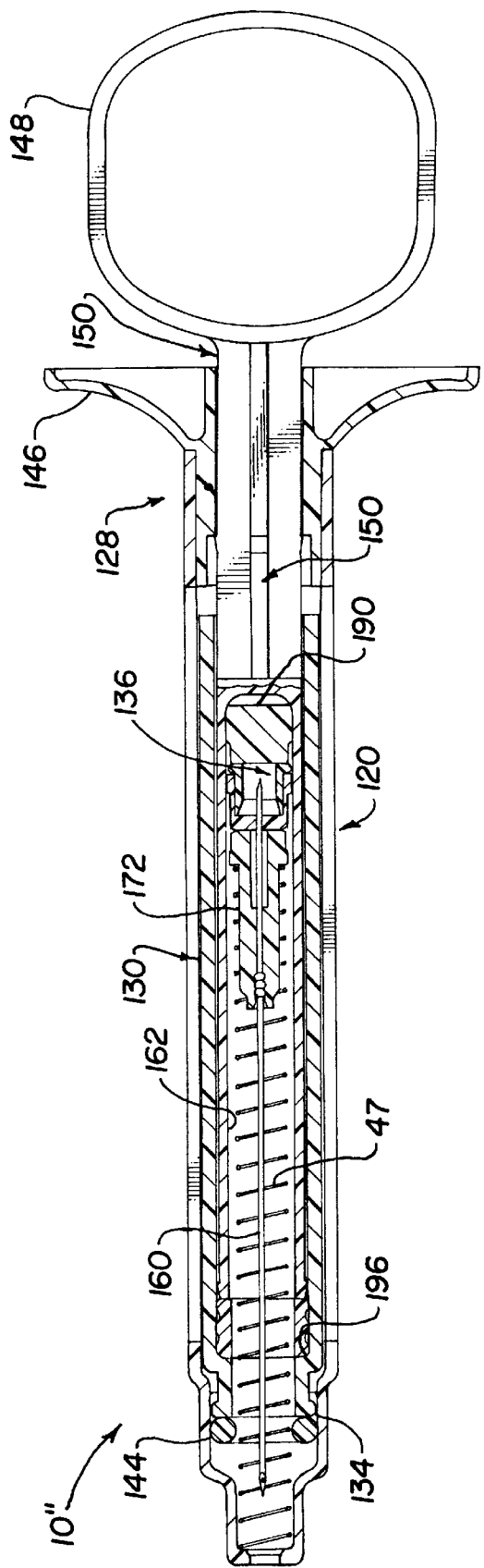
FIG. 13 shows the retracted position of the device of FIGS. 10–12 upon further depression of the plunger from the position of FIG. 12.

In FIG. 13, retraction has occurred by movement of the plunger forward together with carpule 130 after the end-of-injection position of FIGS. 11 and 12 has been reached. Visualized from the perspective of FIG. 12, it is seen that movement of the carpule in the needle direction preferably first begins sliding the front seal and core portion of the rear seal rearwardly with respect to the carpule a short distance until front 134 of carpule 130 presses against ring member 144 (in this case an "O" ring) which is forced to compress and move forward relative to the housing until the needle holder and needle are released to enter into the hollow tubular portion 162 of plunger 150 inside carpule 130, all of which are contained in fluid chamber 158. The expansion of spring 47 upon release of the needle holder and the near simultaneous opening in the mouth of the carpule allows the needle holder and needle to be driven into the carpule where the needle is safe.

FIG. 12A illustrates a variation of the structure just described. A slightly modified form of a retractably mounted needle structure 140 is structure 140'. Rear seal 138 and front seal 136 are slidingly mounted respectively in carpule 130 and opening 202 of mouth 134 as in the previous figures. Needle 160 is still fixed in needle body portion 172 which is bottomed in the front 200 of housing 120. Spring 47 is compressed under a widened head portion 204 which has a linearly oriented surface 205 which is preferably circular and in contact with a linear surface 206 on a disc like separable member 208 which is preferably frictionally held onto head 204 to prevent premature retraction. The inner surface of reduced diameter front portion 142 of the housing may contain an annular constriction 210 (which may be segmented) which in addition to the friction from slightly rounded outer surface 212 holds a combined needle holder and removable part in the retracted position. The friction engagement at the cooperating frictional surfaces 205, 206 can be controlled by the inside diameter of the disc 208 in relation to the outside diameter of the widened portion 204. The device of FIG. 12A functions substantially the same as the device of FIGS. 10–13 in that the needle holder grounded in the front of the housing serves as an obstacle when the plunger is depressed to move the carpule forward wherein the mouth of the carpule removes the ring member 208 and the needle is released for retraction into the carpule.

Figure 14:
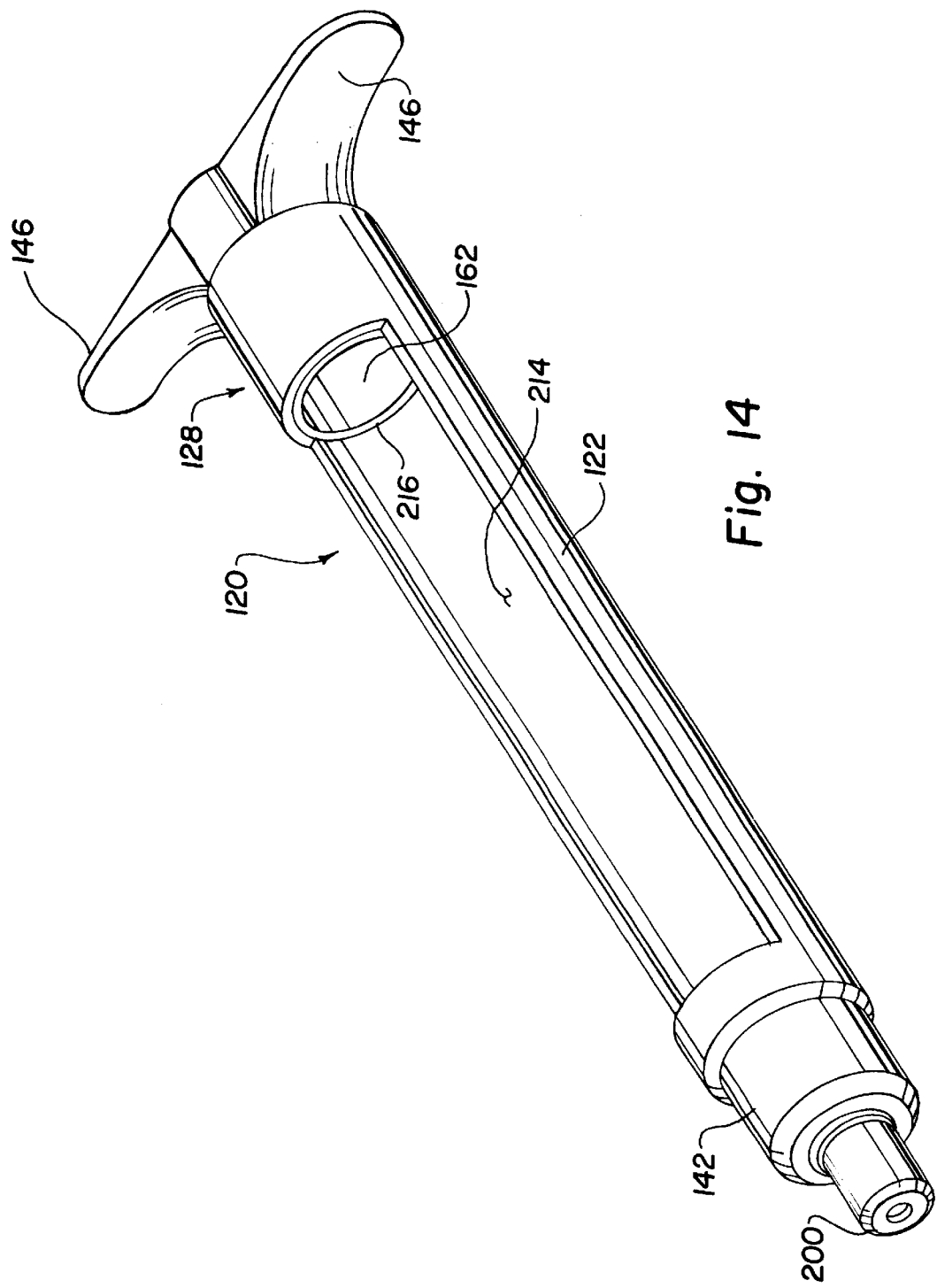
FIG. 14 is a perspective view of the elongated tubular housing having an opening in the side adapted to accept a carpule.

FIG. 14 is a perspective view showing the tubular housing 120 has an opening 214 in wall 122 which is adapted to receive carpule 130 from the previous figures. It also indicates that the rim portion 146 can be separately attached at the rear 128 of the housing to create a lip 216 which may serve to catch hooked front 156 of plunger 150 if it is attempted to be withdrawn after retraction.

In the best mode, the carpule is glass and the housing and plunger are conventional syringe plastics. The sliding front seal and rim member are preferably rubber of a medical grade having long shelf life without interacting with medication. Likewise, the core member is glass or a hard plastic which will not react with desired medications. The push ring and needle holder are preferably polypropylene selected to be semi-rigid with a limited amount of flexibility for use in the alternate embodiment.

Although the invention has been disclosed above with regard to a particular and preferred embodiment, which is advanced for illustrative purposes only, it is not intended to limit the scope of this invention. It will be appreciated that various modifications, alternatives, variations, etc., may be made without departing from the spirit and scope of the invention as defined in the appended claims.

What is claimed:

1. A retractable dental syringe, comprising:
   a carpule having a fluid chamber and a front seal and a rear seal for holding fluid in the chamber;

a tubular housing which accepts the carpule, the tubular housing having a front end portion holding a retractably mounted needle in fluid communication with the fluid chamber for dispensing fluid contents of the carpule;

a depressible plunger which presses against the rear seal to dispense fluid from the carpule; and the carpule being adapted to release and receive the retractably mounted needle once the fluid id dispensed as the plunger and the carpule are moving forward in response to depression of the plunger.

2. The dental syringe of claim 1 wherein the tubular housing has an open side through which the carpule is accepted.

3. The dental syringe of claim 1 wherein the needle is retractably mounted by means of a ring member in combination with a needle holder.

4. The dental syringe of claim 3 wherein moving the carpule releases and receives the needle by moving the ring member and relatively moving the front seal thereby freeing the needle holder to pass into the fluid chamber of the carpule.

5. The dental syringe of claim 3 whereby the needle holder is mounted in the front of the tubular housing and whereby movement of the carpule in response to the plunger causes the front seal to be dislodged by the needle holder thereby creating an open space so that the needle holder can retract the needle into the carpule.

6. The dental syringe of claim 1 wherein the carpule has a mouth which is adapted to release and receive the retractably mounted needle once the fluid is dispensed in response to further depression of the plunger.

7. The dental syringe of claim 6 wherein the tubular housing and depressible plunger are provided with catches to keep the plunger in the housing after the needle is retracted into the carpule.

8. The dental syringe of claim 6 wherein the carpule has a tubular wall which defines the fluid chamber and the depressible plunger has a front portion comprising an elongated tubular wall portion which slides in proximity to the wall of the carpule inside the carpule.

9. The dental syringe of claim 1 wherein the rear seal comprises a slidable separable two-part seal comprising a core part and a rim part and wherein the depressible plunger presses against the rim part.

10. The dental syringe of claim 9 wherein the syringe is emptied by depressing the plunger until the two-part seal is moved to the front end portion of the tubular housing and whereupon further depression of the plunger moves the carpule in a direction towards the needle without moving the core part of the two-part seal whereby an opening is created for retraction of the needle into the carpule.

11. A retractable dental syringe, comprising:

a tubular housing adapted to accept a carpule, the tubular housing having a front portion, an intermediate portion and a rear portion;

a carpule having a fluid chamber, a front seal and a rear seal for enclosing fluid in the chamber, the carpule having a mouth in front and being sized to fit said housing;

a depressible plunger which empties the carpule by moving the rear seal forward to an end-of-injection position;

needle structure in fluid communication with the carpule, the needle structure being retractably mounted in the front of the housing for retraction into the carpule;

whereby the mouth of the carpule is adapted to release the retractable needle for retraction into the carpule in response to depression of the plunger beyond the end-of-injection position of the plunger.

12. The dental syringe of claim 11 wherein the carpule is positionable for use in the intermediate portion of the tubular housing.

13. The dental syringe of claim 12 wherein the carpule is sized to substantially occupy the intermediate portion of the housing.

14. The dental syringe of claim 13 wherein cooperating catches are provided on the housing and the depressible plunger to keep the plunger in the housing after the plunger reaches the end-of-injection position.

15. The dental syringe of claim 11 wherein the carpule has a tubular wall which forms the fluid chamber and wherein the depressible plunger has a front portion comprising an elongated tubular wall portion which slides in proximity to the wall of the fluid chamber inside the carpule.

16. The dental syringe of claim 15 wherein the carpule may be installed and removed through the side of the housing.

17. The dental syringe of claim 11 wherein the needle structure comprises a hard part which holds a needle and a releasable part which holds the hard part in position.

18. The dental syringe of claim 17 wherein the mouth of the carpule moves the releasable part forward after the end-of-injection position is reached during continued depression of the plunger.

19. The dental syringe of claim 18 wherein the releasable part that is moved by the mouth of the carpule comprises an "O" ring.

20. The dental syringe of claim 18 wherein the releasable part comprises a ring member which frictionally engages the hard part of the needle structure along a substantial common interface.

21. A method of operating a syringe, comprising:

providing an elongated tubular housing having a front portion containing a retractable needle structure having a retractable needle holding part and a separable part which releases the needle holding part and needle for retraction;

providing a carpule for the tubular housing, the carpule having a mouth in front with a front seal and a back portion with a slidable and separable two-part seal, the carpule having a fluid chamber between said seals in fluid communication with the needle;

providing a depressible plunger having a tubular front portion in pressing contact with one part of the separable two-part seal;

depressing the plunger to move the two-part seal forward to a sufficient extent as to expel substantially all fluid from the fluid chamber through the needle; and moving the carpule toward the needle structure in response to additional depression of the plunger to thereby automatically retract the needle holding part into the carpule through the mouth of the carpule.

22. The method of claim 21, wherein the step of moving the carpule toward the needle structure is accompanied by the steps of:

moving the separable part relative to the needle holding part, and moving one part of the separable two-part seal relative to the other part of said seal.

23. The method of claim 22 wherein the step of moving the carpule toward the needle structure includes the step of moving the front seal from the mouth of the carpule in a direction away from the needle holding structure.

24. The method of claim 21 wherein:

the step of providing a needle holding structure includes the step of providing a separable part comprising a ring member; and the step of automatically retracting the needle holding part into the carpule includes the step of separating the ring member from the needle holding part.

25. The method of claim 23 wherein the step of moving the front seal out of the mouth of the carpule includes the step of moving the front seal relative to said other part of the separable two-part seal in a direction away from the needle holding structure.

* * * * *